United States Patent
Kim et al.

(10) Patent No.: US 9,114,155 B2
(45) Date of Patent: Aug. 25, 2015

(54) COMPOSITION CONTAINING JETBEAD EXTRACTS

(75) Inventors: Won Gon Kim, Daejeon (KR); Baek Soo Han, Daejeon (KR); Kyoung Shim Kim, Daejeon (KR); Kwang Soo Kim, Daejeon (KR); Young Mi Kang, Daejeon (KR); Chun Hyung Kim, Lexington, MA (US); Mi Jin Sohn, Daejeon (KR); Hoe Yune Jung, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 193 days.

(21) Appl. No.: 14/009,596

(22) PCT Filed: Apr. 6, 2012

(86) PCT No.: PCT/KR2012/002653
§ 371 (c)(1),
(2), (4) Date: Dec. 24, 2013

(87) PCT Pub. No.: WO2012/138190
PCT Pub. Date: Oct. 11, 2012

(65) Prior Publication Data
US 2014/0370132 A1  Dec. 18, 2014

(30) Foreign Application Priority Data
Apr. 6, 2011 (KR) .................. 10-2011-0031615

(51) Int. Cl.
*A61K 36/73* (2006.01)
*A61K 36/738* (2006.01)

(52) U.S. Cl.
CPC .............. *A61K 36/73* (2013.01); *A61K 36/738* (2013.01)

(58) Field of Classification Search
None
See application file for complete search history.

(56) References Cited

U.S. PATENT DOCUMENTS

| 3,837,834 | A | * | 9/1974 | Hill et al. ....................... 504/175 |
| 5,604,208 | A | * | 2/1997 | Alvarado-Licon .............. 514/40 |
| 2008/0160059 | A1 | * | 7/2008 | Alvarado Licon ............ 424/417 |
| 2011/0191902 | A1 | * | 8/2011 | Atkinson et al. .............. 800/278 |
| 2012/0023616 | A1 | * | 1/2012 | Nishimura et al. ........... 800/278 |

FOREIGN PATENT DOCUMENTS

| KR | 10-2001-0081188 A | 8/2001 |
| KR | 10-2004-0012396 A | 2/2004 |
| KR | 10-2004-0029072 A | 4/2004 |
| KR | 10-2008-0032127 A | 4/2008 |
| KR | 10-2009-0102136 A | 9/2009 |
| KR | 10-2010-0060123 A | 6/2010 |
| KR | 10-2010-0060949 A | 6/2010 |
| KR | 10-2011-0013466 | 2/2011 |

OTHER PUBLICATIONS

International Search Report, PCT/KR2012/002653, Korean Intellectual Property Office, Oct. 30, 2012.

* cited by examiner

*Primary Examiner* — Chris R Tate
*Assistant Examiner* — Randall Winston
(74) *Attorney, Agent, or Firm* — Joseph R. Baker, Jr.; Gavrilovich, Dodd & Lindsey LLP

(57) ABSTRACT

The present invention relates to a pharmaceutical composition for preventing or treating Parkinson's disease, which comprises, as an active ingredient, a *Rhodotypos scandens* extract obtained by extracting the stem of *Rhodotypos scandens* with an organic solvent, and a food additive showing the effect of preventing or treating Parkinson's disease, the food additive comprising *Rhodotypos scandens* extract as an active ingredient. The *Rhodotypos scandens* extracts of the present invention may prevent or treat Parkinson's disease without producing any particular side effects, and therefore can be widely used for more safely treating Parkinson's disease.

5 Claims, 1 Drawing Sheet

COMPOSITION CONTAINING JETBEAD EXTRACTS

This application is a U.S. National Stage Application filed under 35 U.S.C. §371 and claims priority to International Application No. PCT/KR2012/002653, filed Apr. 6, 2012, which application claims priority under 35 U.S.C. §119 to Korean Application No. 10-2011-0031615, filed Apr. 6, 2011, the disclosures of which are incorporated herein by reference.

TECHNICAL FIELD

The present invention relates to a composition comprising a *Rhodotypos scandens* extract, and more particularly to a pharmaceutical composition for preventing or treating Parkinson's disease, which comprises as an active ingredient a *Rhodotypos scandens* extract obtained by extracting the stem of *Rhodotypos scandens* with an organic solvent, and to a food additive showing the effect of preventing or treating Parkinson's disease, the food additive comprising *Rhodotypos scandens* extract as an active ingredient.

BACKGROUND ART

Neurodegenerative diseases are associated with conditions in which neurons degenerate, lose their function, and often die. Because these diseases are generally progressive, the consequences of neurodegenerative diseases are often very devastating. Patients with neurodegenerative disease may undergo severe deterioration in cognitive or motor skills. As a result, the quality of life and life expectancy of the patients may be considerably reduced. In humans, these diseases include, but are not limited to, Alzheimer's disease, Parkinson's disease, amyotrophic lateral sclerosis, Huntington's disease, fronto-temporal dementia, and cortico basal degeneration, and other diseases.

Particularly, Parkinson's disease is a chronic progressive neurodegenerative disease that affects brain neurons that control muscle movement. It occurs when cells that produce the neurotransmitter dopamine in substantia nigra are damaged suddenly or degenerated or the number thereof greatly decreases. Because the dopamine is an important chemical that is involved in intracellular signaling for facilitating body movement, motor syndromes, including tremor, rigidity, bradykinesia, postural instability and akinesia, typically occur in the case of Parkinson's disease. Although the cause of damage to the dopamine-producing cells has not yet been clearly determined, it is known that damage to these cells is related to cerebral arteriosclerosis, carbon-monoxide poisoning, medication, metabolic or traumatic encephalitis sequelae induced by hypoparathyroidism, etc.

Known drugs for treating Parkinson's disease include L-dopa drugs, dopamine receptor agonists, anti-cholinergic drugs, Eldepryl (or depreyl), etc. Most of these drugs do not provide causal treatment of Parkinson's disease, but act to control conditions, and thus need to be administered continually. However, the long-term administration of such drugs causes side effects. For example, anti-cholinergic drugs may cause autonomic nervous system abnormalities or abnormal mental functions, and for this reason, continuous administration thereof to aged patients is limited. In addition, in the case of L-dopa drugs, the long-term administration thereof leads to a gradual decrease in the effect and causes side effects, including abnormal movements such as body twisting, or spontaneous movement of the hands or feet.

In order to prevent such side effects, efforts have been actively made to develop natural material-derived agents for treating Parkinson's disease. For example, Korean Patent Laid-Open Publication No. 2001-0081188 discloses a composition for preventing and treating brain diseases and neural diseases, including Parkinson's disease and senile dementia, the composition comprising, as an active ingredient, a Scutellariae radix extract having the effect of protecting neurons. Korean Patent Laid-Open Publication No. 2004-0012396 discloses a composition for treating neurodegenerative diseases such as Parkinson's disease and paralysis, the composition comprising an extract of *Beauveria bassiana* 101A. Korean Patent Laid-Open Publication No. 2004-0029072 discloses a pharmaceutical composition for treating Parkinson's disease, which comprises an extract obtained from the bark of *Wenguanguo*. Korean Patent Laid-Open Publication No. 2010-0060123 discloses a pharmaceutical composition for preventing or treating Parkinson's disease, which comprises a ginger extract or shogaol. Korean Patent Laid-Open Publication No. 2010-0060949 discloses a neuron-protecting composition for preventing or treating diseases such as Parkinson's disease, which comprises a peach leaf extract as an active ingredient. Korean Patent Laid-Open Publication No. 2011-0013466 discloses a pharmaceutical composition for treating Parkinson's disease, which comprises, as an active ingredient, a grape seed extract or one or more compounds derived therefrom. These components derived from natural materials have no side effects, but have a shortcoming in that the efficiency of treatment of Parkinson's disease is low.

DISCLOSURE

Technical Problem

The present inventors have found that an extract from the stem of *Rhodotypos scandens* that is a natural material has an excellent effect of treating Parkinson's disease while having no side effects, thereby completing the present invention.

Technical Solution

It is an object of the present invention to provide a pharmaceutical composition for preventing or treating Parkinson's disease, the composition comprising a *Rhodotypos scandens* extract.

Another object of the present invention is to provide a food additive showing the effect of preventing or treating Parkinson's disease, the composition comprising the *Rhodotypos scandens* extract.

Advantageous Effects

The *Rhodotypos scandens* extract of the present invention can prevent or treat Parkinson's disease without causing side effects, and thus can be widely used for safer treatment of Parkinson's disease.

BEST MODE

To achieve the above objects, in one aspect, the present invention provides an extract from the stem of *Rhodotypos scandens*, which can exhibit the effect of preventing and treating Parkinson's disease.

As used herein, the term "*Rhodotypos scandens*" refers to a dicotyledonous deciduous shrub belonging to the family Rosaceae of the order Rosales of *Archichlamydeae*. In Korea, it grows mainly on the seashore, but is also rarely distributed in inland areas, including Yeongwol-gun, Gangwon-do. In Chinese medicine, the root of *Rhodotypos scandens* is used for the treatment of anemia.

As used herein, the term "*Rhodotypos scandens* extract" refers to an extract obtained from *Rhodotypos scandens*, preferably an extract obtained from the stem of *Rhodotypos scandens*, more preferably an extract obtained by extracting the stem of *Rhodotypos scandens* with an organic extract, and even more preferably an extract obtained by extracting the stem of *Rhodotypos scandens* with a $C_1$-$C_5$ lower alkyl alcohol.

Figure 1:
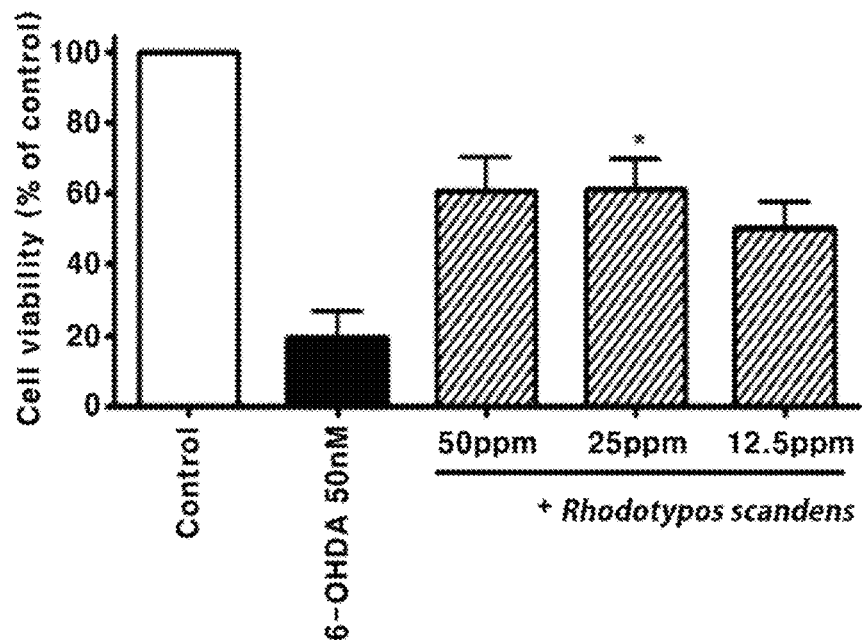
FIG. 1 is a graphic diagram showing the effects of varying concentrations of a *Rhodotypos scandens* extract against neuronal cell death that is induced by 6-OHDA.

The present inventors have conducted studies on various types of extracts obtained from various natural materials in order to find natural material-derived components that have an excellent effect of preventing or treating Parkinson's disease while having no side effect. As a result, the present inventors have found that the *Rhodotypos scandens* extract exhibits an effect of preventing neurons from being damaged by compounds (e.g., 6-OHDA, etc.) known to kill neurons (FIG. 1).

Figure 2:
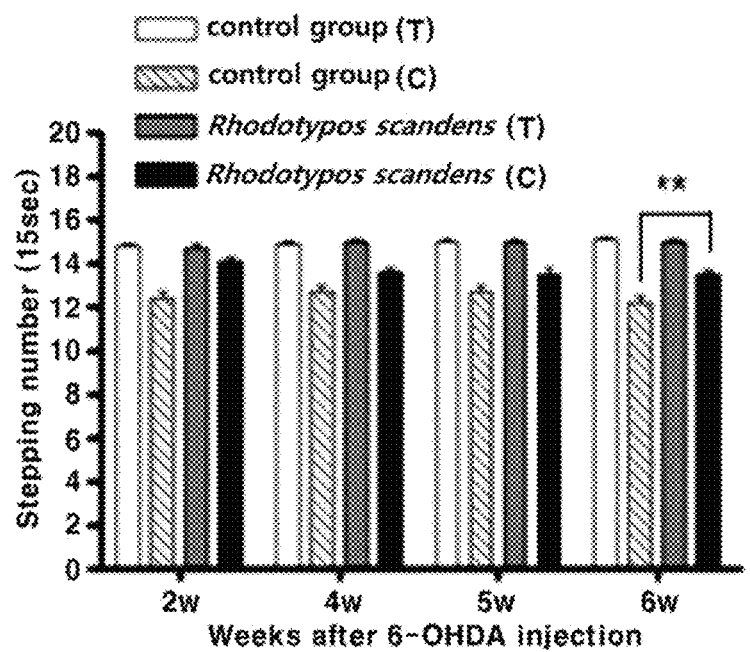
FIG. 2 is a graphic diagram showing the results of a stepping test conducted to measure the effect of the *Rhodotypos scandens* extract on rats with killed dopaminergic neurons.

In addition, the present inventors killed the dopaminergic neurons of the brain in rats and fed the rats with a mixture of the *Rhodotypos scandens* extract and feed, and as a result, it could be seen that the neural functions damaged by the killed dopaminergic neurons were slowly improved (FIG. 2).

Thus, it could be seen that the *Rhodotypos scandens* extract showed an effect on the prevention or treatment of Parkinson's disease.

In another aspect, the present invention provides a pharmaceutical composition for preventing or treating Parkinson's disease, which comprises the *Rhodotypos scandens* extract as an active ingredient together with a pharmaceutically acceptable carrier.

As used herein, the term "pharmaceutically acceptable carrier" refers to a carrier or diluent that does not cause irritation to an organism and does not abrogate the biological activity and properties of the administered compound. When the composition is formulated into a liquid solution, the pharmaceutically acceptable carrier may be one or more of saline, sterile water, Ringer's solution, buffered saline, albumin injection solution, dextrose solution, maltodextrin solution, glycerol, and ethanol, which are sterile and biocompatible. If necessary, other conventional additives, including an antioxidant, a buffer and a bacteriostatic agent, may be added to the composition.

In still another aspect, the present invention provides a method of treating Parkinson's disease using the *Rhodotypos scandens* extract.

The treating method may be a method comprising administering the pharmaceutical composition to a subject in need of treatment. Herein, the *Rhodotypos scandens* extract, the carrier and Parkinson's disease are as described above.

The composition may be administered in a pharmaceutically effective amount in a single or multiple dosage form. Herein, the composition may be administered in the form of liquid, powder, aerosol, capsule, enteric coated tablet or capsule, or suppository. In addition, the composition may be administered intraperitoneally, intravenously, intramuscularly, subcutaneously, intradermally, orally, topicallly, intranasally, intrapulmonarily or intrarectally, but is not limited thereto. However, when the composition is administered orally, the *Rhodotypos scandens* extract derived from a natural material can be lost due to digestion in the stomach, and for this reason, the oral composition should be formulated so that the active ingredient is coated or protected from decomposition in the stomach. In addition, the pharmaceutical composition may be administered using any system capable of delivering the active ingredient to a target cell. Moreover, the composition for treating Parkinson's disease of the present invention may be administered alone or in combination with other therapeutic agents, and may be administered sequentially or simultaneously with conventional therapeutic agents.

The composition comprising the *Rhodotypos scandens* extract of the present invention is administered in a pharmaceutically effective amount. As used herein, the term "pharmaceutically effective amount" refers to an amount sufficient to treat or prevent diseases, at a reasonable benefit/risk ratio applicable to any medical treatment or prevention. The effective dosage level of the composition may be determined depending on the severity of the disease, the activity of the drug, the patient's age, weight, physical condition and sex, the patient's sensitivity to the drug, the time of administration of the inventive composition used, the route of administration of the composition, the excretion rate, the duration of treatment, drugs combined or used in combination with the composition, and other factors well known in the medical field.

In still another aspect, the present invention provides a food additive for preventing or ameliorating Parkinson's disease, which contains the *Rhodotypos scandens* extract as an active ingredient.

The *Rhodotypos scandens* extract is derived from the natural material, and thus has verified safety. Thus, when the *Rhodotypos scandens* extract is usually eaten according to usual eating habits for a long period of time, it can exhibit the effects of preventing Parkinson's disease and ameliorating the conditions of Parkinson's disease developed.

When the *Rhodotypos scandens* extract of the present invention is used as a food additive, it may be added alone to foods or beverages or used in combination with other food additives. When the food additive for ameliorating Parkinson's disease is added in the preparing process of a food or a beverage, it may be added in an amount of 1-5 wt %, preferably 1-3 wt %, based on the weight of the final food, but is not specifically limited thereto. However, when the food additive is taken for the purpose of health and hygiene or health control for a long period of time, it may be used in an amount smaller than the lower limit of the above range. Further, the active ingredient may also be used in an amount larger than the upper limit of the above range, because it is not problematic in terms of safety.

Examples of the above food or beverage include, but are not limited to, meats, sausages, bread, chocolate, candies, snacks, confectionery, pizza, noodles, gum, dairy products including ice cream, various soups, beverages, teas, drinks, alcoholic beverages and multi-vitamin preparations.

When the food additive comprising the *Rhodotypos scandens* extract of the present invention is added to a food, it may be added together with various auxiliary components, including nutrients, vitamins, electrolytes, flavoring agents, colorants, pectic acid and its salt, alginic acid and its salt, organic acids, protective colloidal thickeners, pH adjusting agents, stabilizers, preservatives, glycerin, alcohols, and the like. The content of the auxiliary components is not specifically limited, but is preferably 0.01-0.1 wt % based on the weight of the final food.

In addition, when the food additive comprising the *Rhodotypos scandens* extract of the present invention is added to a beverage, the beverage may additionally contain various sweetening agents or natural carbohydrates, which are contained in conventional beverages. Herein, examples of the sweeteners include, but are not limited to, natural sweeteners such as thaumatin and stevia extracts, and synthetic sweeteners such as saccharin and aspartame. Examples of the natural carbohydrates include, but are not limited to, monosaccharides (e.g., glucose, fructose, etc.), disaccharides (e.g., maltose, sucrose, etc.), polysaccharides (e.g., dextrin, cyclodextrin, etc.), or sugar alcohols (e.g., xylitol, sorbitol, erythritol, etc.). The content of the natural carbohydrates is not specifically limited, but is preferably about 0.01-0.04 g, and more preferably about 0.02-0.03 g, based on 100 ml of the final beverage.

Mode For Invention

Hereinafter, the present invention will be described in further detail with reference to examples. It is to be understood, however, that these examples are for illustrative purposes only and are not intended to limit the scope of the present invention.

EXAMPLE 1

Preparation of *Rhodotypos scandens* Extract 13.16 kg of the stem of *Rhodotypos scandens* was finely cut, immersed in 25 l of methanol for 4 hours, and filtered to separate it into a solid and a first liquid component. The separated solid was immersed in 25 l of methanol for 4 hours, and filtered to obtain a second liquid component. The obtained first liquid component and second liquid component were mixed with each other, and the mixture was concentrated under reduced pressure. The residue was freeze-dried, thereby obtaining 440 g of a *Rhodotypos scandens* extract.

EXAMPLE 2

Effect of *Rhodotypos scandens* Extract on SH-SY5Y Cells

SH-SY5Y neuronal cells were seeded into a 24-well plate at a density of $5 \times 10^5$ cells/well and cultured in a $CO_2$ incubator for 24 hours. The cultured cells were treated with 50 μM of 6-OHDA (cell death inducer) alone or together with different concentrations of the *Rhodotypos scandens* extract and incubated in a 5% $CO_2$ incubator at 37° C. for 24 hours. After 24 hours, each well of the plate was treated with 1 mg/ml of MTT solution and stored in a 5% $CO_2$ incubator for 1 hour, and then MTT extraction solution was added thereto. Then, the plate was stored at 37° C. for 24 hours, and the absorbance of each well at 570 nm was measured (FIG. 1). FIG. 1 is a graphic diagram showing the effects of varying concentrations of the *Rhodotypos scandens* extract against neuronal cell death that is induced by 6-OHDA. As can be seen in FIG. 1, neuronal cell death that is induced by 6-OHDA was inhibited by the *Rhodotypos scandens* extract.

EXAMPLE 3

Effect of *Rhodotypos scandens* Extract on Rats with Damaged Neurons

To specifically kill the dopaminergic neuronal cells in the substantia nigra of a 6-week-old SD rat (Core Tech Co., Ltd.), 8 μg of 6-OHDA (1 μg/μl) was injected directly into the AP (−4.3), ML (−1.8) and DV (−8.2) site and AP (−5.0), ML (−1.8) and DV (−8.2) site of the cerebral left hemisphere at a rate of 1 μl/min using an injection kit (stereotaxic tool). At 30 minutes before the administration of 6-OHDA, desipramine was administered to the rats at a dose of 25 mg/kg to inhibit the death of cells other than the dopaminergic neuronal cells. Next, the rat was fed with feed containing the *Rhodotypos scandens* extract for 2 weeks in such a manner that the daily dose of the *Rhodotypos scandens* extract was 500 mg/kg. As a control group, a rat fed with feed containing no *Rhodotypos scandens* extract was used.

A stepping test that is a non-pharmacological test method having reduced error compared to a pharmacological test method was carried out. Specifically, in a state in which three legs of the rat, excluding the left hind leg, were controlled by hand, the rat was allowed to move on a 90 cm-long table for 15 seconds while the number of steps of the left hind leg on the table surface was repeatedly counted three times. In addition, in a state in which three legs of the same rat, excluding the right hind leg, were controlled by hand, the rat was allowed to move on the table for 15 seconds while the number of steps of the right hind leg on the table surface were repeatedly counted three times.

The number of steps was counted at 3 days before injection of 6-OHDA and 2 weeks, 4 weeks, 5 weeks and 6 weeks after injection of 6-OHDA (FIG. 2). FIG. 2 is a graphic diagram showing the results of the stepping test carried out to measure the effect of the *Rhodotypos scandens* extract on the rats with killed dopaminergic neurons. In FIG. 2, the control group (T) indicates the results of a stepping test conducted on the left hind leg of a rat fed with feed containing no *Rhodotypos scandens* extract; the control group (C) indicates the results of a stepping test conducted on the right hind leg of the rat fed with feed containing no *Rhodotypos scandens* extract; the *Rhodotypos scandens* (T) indicates the results of a stepping test conducted on the left hind leg of a rat fed with feed containing the *Rhodotypos scandens* extract; and the *Rhodotypos scandens* (C) indicates the results of a stepping test conducted on the right hind leg of the rat fed with feed containing the *Rhodotypos scandens* extract.

As can be seen in FIG. 2, in both the rat (control group) fed with feed containing no *Rhodotypos scandens* extract and the rat (test group) fed with feed containing the *Rhodotypos scandens* extract, the right hind legs (control group (C) and *Rhodotypos scandens* (C)) that are influenced by the cerebral left hemisphere injected with 6-OHDA showed a relatively small stepping number compared to the left hind legs (control group (T) and *Rhodotypos scandens* ((T)) that are influenced by the cerebral right hemisphere injected with no 6-OHDA. This result suggests that the neuronal cells of the brain was damaged by injection of 6-OHDA.

In addition, it could be seen that the left hind legs (control group (T) and *Rhodotypos scandens* (T)) that are influenced by the cerebral right hemisphere injected with no 6-OHDA showed the same stepping number regardless of whether or not the rats were fed with the *Rhodotypos scandens* extract, whereas the right hind legs (control group (C) and *Rhodotypos scandens* (C)) that are influenced by the cerebral left hemisphere injected with 6-OHDA showed a significant increase in the stepping number as a result of feeding with the *Rhodotypos scandens* extract, but the stepping number of the right hind legs was smaller than that of the left hind legs. These results suggest that the *Rhodotypos scandens* extract inhibited the neuronal cells of the brain from being damaged by 6-OHDA.

The invention claimed is:

1. A method for treating Parkinson's disease in a subject in need thereof, the method comprising administering a composition comprising an effective amount of a *Rhodotypos scandens* extract to the subject.

2. The method of claim 1, wherein the *Rhodotypos scandens* extract is an extract of a stem of *Rhodotypos scandens*.

3. The method of claim 2, wherein the *Rhodotypos scandens* extract is an organic solvent extract of the stem of *Rhodotypos scandens*.

4. The method of claim 3, wherein the organic solvent is a $C_1$-$C_5$ lower alkyl alcohol.

5. The method of claim 4, wherein the $C_1$-$C_5$ lower alkyl alcohol is methanol.

* * * * *